US008025700B2

(12) United States Patent  (10) Patent No.: US 8,025,700 B2
Samain et al.  (45) Date of Patent: Sep. 27, 2011

(54) METHOD AND SYSTEM FOR OPTICALLY BLEACHING KERATINOUS FIBERS

(75) Inventors: Henri Samain, Bievres (FR); Patricia Fridelance, Saint-Vallier de Thiey (FR)

(73) Assignee: L'Oreal, Paris (FR)

( * ) Notice: Subject to any disclaimer, the term of this patent is extended or adjusted under 35 U.S.C. 154(b) by 877 days.

(21) Appl. No.: 11/587,360

(22) PCT Filed: May 3, 2005

(86) PCT No.: PCT/IB2005/001193
§ 371 (c)(1),
(2), (4) Date: Mar. 19, 2007

(87) PCT Pub. No.: WO2005/104897
PCT Pub. Date: Nov. 10, 2005

(65) Prior Publication Data
US 2007/0167936 A1  Jul. 19, 2007

Related U.S. Application Data

(60) Provisional application No. 60/579,242, filed on Jun. 15, 2004.

(30) Foreign Application Priority Data

May 4, 2004 (FR) ..................................... 04 04784

(51) Int. Cl.
*D06L 3/04* (2006.01)
(52) U.S. Cl. ................. 8/103; 8/101; 8/115.52
(58) Field of Classification Search .............. 8/101, 102, 8/103, 115.52, 409
See application file for complete search history.

(56) References Cited

U.S. PATENT DOCUMENTS

| 3,916,143 | A | * | 10/1975 | Farrell ..................... 219/121.69 |
| 4,792,341 | A | | 12/1988 | Kozikowski et al. |
| 5,246,019 | A | | 9/1993 | Godfrey et al. |
| 5,303,722 | A | | 4/1994 | Godfrey et al. |
| 5,679,113 | A | * | 10/1997 | Caisey et al. ..................... 8/103 |
| 5,725,600 | A | * | 3/1998 | Caisey et al. ..................... 8/103 |
| 5,906,610 | A | | 5/1999 | Mehl, Sr. et al. |
| 6,035,862 | A | * | 3/2000 | Di Luca ....................... 132/270 |

FOREIGN PATENT DOCUMENTS

| DE | 199 42 074 | | 3/2001 |
| EP | 682 937 | | 11/1995 |
| EP | 685 180 | | 12/1995 |
| EP | 685 220 | | 12/1995 |
| FR | 2 719 472 | A | 11/1995 |
| WO | WO 0133991 A1 | * | 5/2001 |
| WO | WO 01/60457 | | 8/2001 |

OTHER PUBLICATIONS

Zhou, Bingkun, Thomas J. Kane, George J. Dixon, and Robert L. Byer. "Efficient, frequency-stable laser-diode-pumped Nd:YAG laser" in Optics Letters, vol. 10, No. 2, Feb. 1985, pp. 62-64.*

* cited by examiner

*Primary Examiner* — Harold Pyon
*Assistant Examiner* — Katie L Hammer
(74) *Attorney, Agent, or Firm* — Oliff & Berridge, PLC

(57) ABSTRACT

The present invention relates to a method of treating keratinous fibers, especially hair fibers, comprising at least one step of at least partially bleaching the fibers, in which at least one region to be treated is exposed to at least one light pulse, characterized in that this pulse is generated by a diode-pumped laser or by a regenerative amplifier laser.

42 Claims, 5 Drawing Sheets

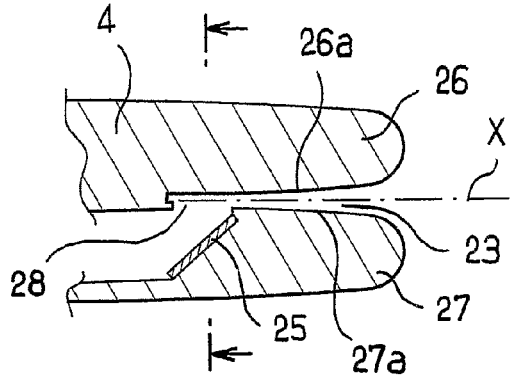
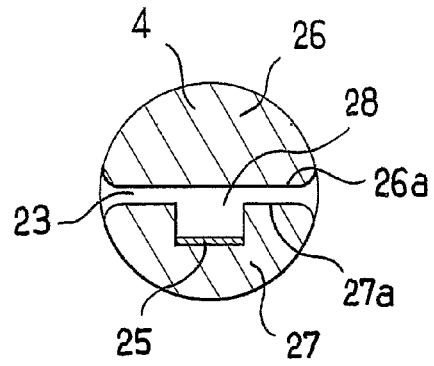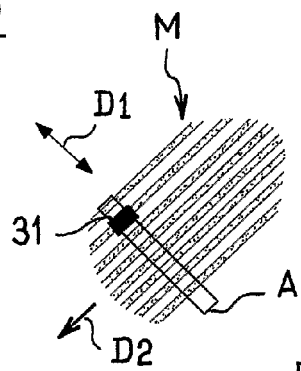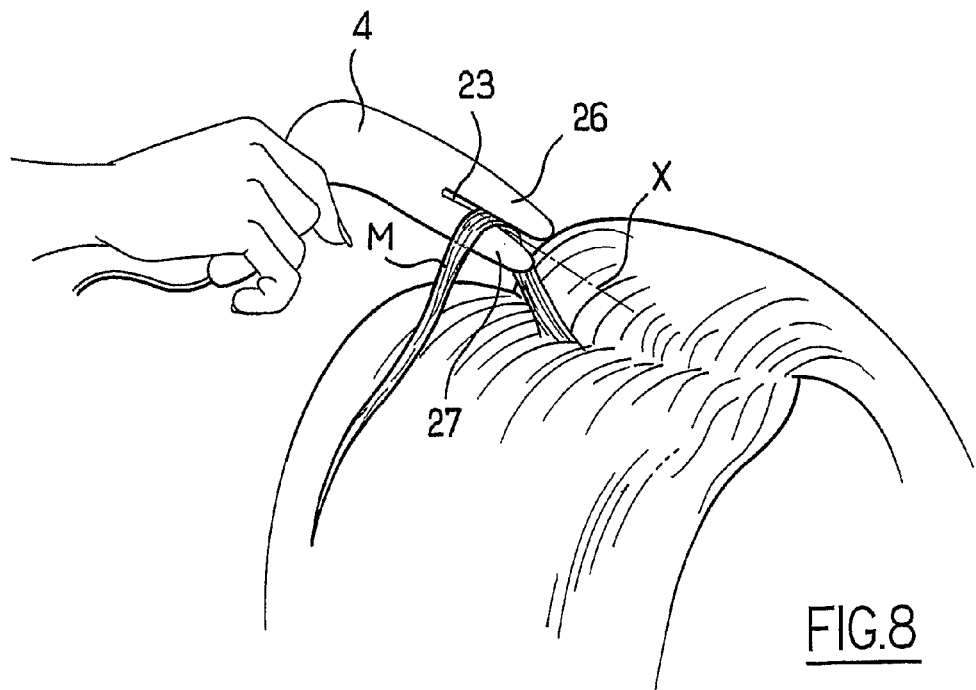

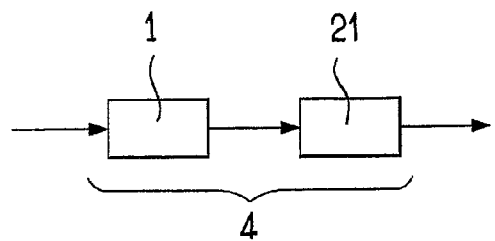
FIG.13
FIG.14
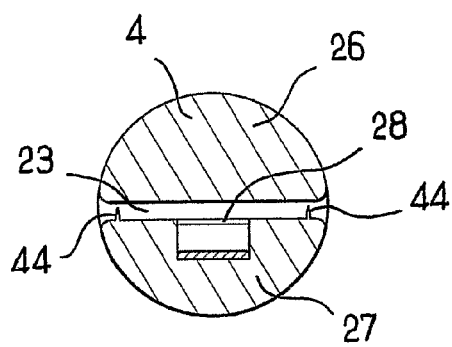
FIG.15
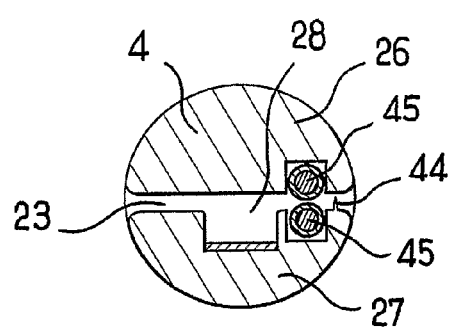
FIG.16
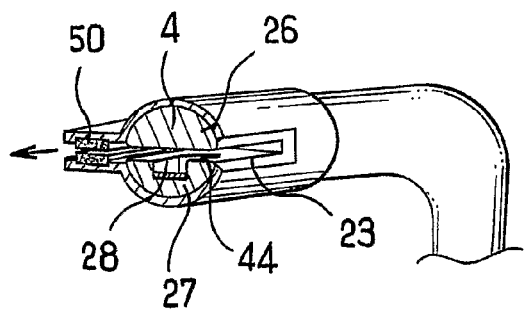
FIG.18
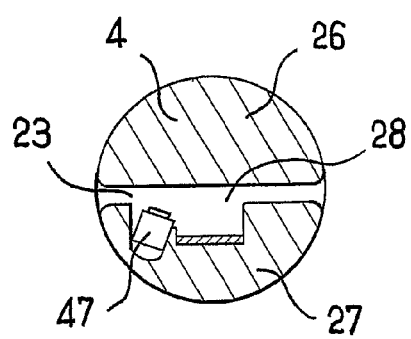
FIG.17

METHOD AND SYSTEM FOR OPTICALLY BLEACHING KERATINOUS FIBERS

The present invention relates to a method and to a system for optically bleaching keratinous fibers, especially hair fibers, by the emission of light radiation.

One difficulty that arises when it is desired to bleach keratinous fibers by exposing them to light radiation is to succeed in destroying the melanin without damaging the rest of the fiber. To do this, the prior art teaches injecting very high power over the shortest time possible.

Thus, optical bleaching methods are known, from European patent applications EP 682 937-A1, EP 685 180-A1 and EP 685 220-A1 and from U.S. Pat. No. 4,792,341, in which the hair is exposed to the light of a flashlamp-pumped laser.

This laser delivers relatively short pulses of very high energy, which are very effective for selectively destroying melanin. However, it does have the drawback of being relatively bulky. Furthermore, the conditions of use of the laser must be relatively precise in order to avoid overheating or damaging the hair by overexposing it to the light emitted by the laser.

U.S. Pat. No. 5,246,019 and U.S. Pat. No. 5,303,722 disclose other methods and devices for bleaching hair.

There exists a need for a method that makes it possible to reduce the risk of damaging the hair and to produce novel effects.

There also exists a need to have an optical bleaching system that is relatively compact and easy to handle.

One subject of the invention is, according to a first of its aspects, a method of treating keratinous fibers, especially hair fibers, comprising at least one step of at least partially bleaching the fibers, in which at least one region to be treated is exposed to at least one light pulse, this pulse being generated by a diode-pumped laser or by a regenerative amplifier laser.

The term "regenerative amplifier laser" is understood to mean a laser comprising a cavity called a mode-locked oscillator, which emits very low-energy pulses at a high frequency, for example of the order of 100 MHz, and a regenerative amplifier that selects, at a relatively low frequency, for example a few kHz, one of these pulses and amplifies it. The pulses obtained may have a duration of between, for example, about 20 ps and a few nanoseconds.

The term "diode-pumped laser" is understood to mean a laser in which the optical pumping is obtained by means of a laser diode, for example at least one "Q-switched" diode.

In a diode-pumped laser, the peak power may be lower and the duration of each pulse longer than in a flashlamp-pumped laser, so it might be expected that this laser is unsuitable for bleaching hair. However, the inventors have been able to demonstrate that the energy could be sufficient to selectively destroy the melanin and to bleach keratinous fibers and that the risk of damaging the hair was reduced on account of the lower power levels employed.

A regenerative amplifier laser has characteristics that are relatively similar to those of a diode-pumped laser.

The emission frequency of the light pulses from a diode-pumped laser may furthermore be higher than that of a flashlamp-pumped laser, which may allow more rapid scanning of the keratinous fibers to be bleached. The duration of the bleaching treatment can therefore be shortened and novel effects may be obtained.

Finally, a diode-pumped laser does not require a very bulky power supply and cooling system. This may prove to be advantageous if it is desired to place such a laser in, for example, a hair salon or beauty salon.

A diode-pumped laser comprises an excitable rod, the shape of which is for example parallelepipedal, especially square in cross section. As a variant, the rod may be cylindrical. This excitable rod may comprise a matrix doped with neodymium ions ($Nd^{3+}$), for example a lithium yttrium fluoride ($LiYF_4$) matrix.

The wavelength of the light reaching the keratinous fibers must allow the fibers to be bleached by selectively destroying the melanin and can be between about 400 nm and about 700 nm, for example between about 400 nm and about 600 nm, or even between about 400 nm and about 550 nm. In one illustrative example, the wavelength of the light reaching the keratinous fibers is around 523 nm.

The wavelength of the light received by the keratinous fibers does not necessarily correspond to that of the light emitted by the laser. For convenience, the excitable rod of the laser may emit with a different wavelength and a frequency converter may be inserted in the path of the light between the excitable rod and the keratinous fibers. It is thus possible to use, for example, a laser having an excitable rod emitting at a wavelength of between 1000 and 1100 nm, for example around 1046 nm, and a frequency doubler for bringing the wavelength of the light reaching the keratinous fibers back to about 523 nm.

Irrespective of the type of laser used—diode pumped or regenerative amplifier—the duration of the light pulse reaching the keratinous fibers may be between about 100 ps and about 1 µs, better still between about 1 ns and about 100 ns, especially greater than 5 ns, for example around 10 ns.

The term "duration of the pulse" is understood to mean the time during which the light power of the radiation emitted by the laser and reaching the keratinous fibers is equal to or greater than one half of its peak power.

The number of light pulses to which any one region of the keratinous fibers is exposed may depend on the surface energy of the radiation that reaches the keratinous fibers, on the color of the fibers and on the desired degree of bleaching.

The light pulse may be a single pulse. The surface energy of the single pulse may then be greater than $0.2\ J/cm^2$, being for example greater than $0.5\ J/cm^2$. The surface energy of the single pulse is preferably less than $30\ J/cm^2$ in order not to damage the keratinous fibers.

Irrespective of the light source used—diode-pumped laser or other such laser—it may prove advantageous to treat the keratinous fibers by exposing them locally to several successive pulses, as this allows in particular a more progressive bleaching treatment and the risk of damaging the keratinous fibers may be further reduced.

For example, it is possible to expose one and same region of keratinous fibers to a number of light pulses ranging between 2 and 10. The surface energy of a pulse may then be equal to or greater than $0.06\ J/cm^2$, being for example equal to or greater than $0.12\ J/cm^2$. The surface energy is, for example, equal to or less than $5\ J/cm^2$.

It is also possible to expose the region to be treated to a number of pulses ranging between 11 and 100. The surface energy of a pulse may then be equal to or greater than $0.12/(\log(f)+1)\ J/cm^2$, for example greater than $0.24/(\log(f)+1)\ J/cm^2$, f being the frequency of the pulses. The surface energy per pulse may also be equal to or less than $6/(\log(f)+1)\ J/cm^2$, for example, equal to or less than $4/(\log(f)+1)\ J/cm^2$.

The number of pulses to which the region to be treated is exposed may also be higher, for example greater than 100.

The surface energy per pulse may then be equal to or greater than $0.06/(\log(f)+1)\ J/cm^2$, preferably equal to or greater than $0.12/(\log(f)+1)\ J/cm^2$. The surface energy per pulse may be equal to or less than $2.4/(\log(f)+1)$ J/cm², for example equal to or less than $1.2/(\log(f)+1)$ J/cm².

The above surface energy values are most particularly suitable for chestnut brown hair and may be corrected according to the initial color of the hair, the surface energy being lower the lighter the hair.

The emission frequency of the light pulses may be chosen especially according to the speed of scanning of the keratinous fibers with the light emitted by a treatment head.

The frequency f of the pulses may for example be greater than about 10 Hz, or even greater than about 1 kHz, being around 10 kHz in one illustrative example.

The peak surface power of a laser pulse emitted by the laser and received by the keratinous fibers may be equal to or less than 100 MW/cm², for example equal to or less than 10 MW/cm² or even equal to or less than 1 MW/cm².

It is possible to determine, for example automatically, in accordance with the initial color of the keratinous fibers to be treated at least one of the following: the number of pulses reaching a given region to be treated; the frequency of the pulses; and the surface energy per pulse. Thus, the darker the hair the higher may be the number of pulses and the surface energy per pulse.

It is also possible to determine, for example, again, automatically, in accordance with the desired color after treatment, at least one of the following: the number of pulses; the frequency of the pulses; and the surface energy per pulse. Thus, the less the degree of bleaching the lower the surface energy may be.

The bleaching treatment may be assisted by a color analysis device.

This color analysis device may be used, for example, to determine the color of the keratinous fibers before treatment, for example so as to determine the number of light pulses needed to achieve the desired bleaching of a given region of the keratinous fibers. The lighter the fibers, the lower this number of pulses may be.

The color analysis device may also be used to determine the moment when a predetermined degree of bleaching has been achieved. This is because, after each pulse the fibers are bleached a little more, so that, by analysing the color of the fibers during the treatment, it is possible to detect the moment when the desired color is achieved.

The color analysis device may comprise for example a color camera or any other appropriate detector.

The shape of the light spot reaching the keratinous fibers during emission of a light pulse may be polygonal, for example approximately square or rectangular, or otherwise. A polygonal shape may prove to be advantageous in order to allow complete scanning of a region to be treated, by juxtaposing the light spots.

At least two different regions of keratinous fibers to be treated may be exposed in succession in various ways.

The light pulses may for example be emitted by a treatment head that is moved relative to the keratinous fibers when the treatment passes from a first treament region to a second one. The emission of the light pulses may then be triggered according to the movement of the treatment head relative to the keratinous fibers, so as for example to ensure the same region of keratinous fibers receiving only a predefined number $d_1$ of pulses at each pass of the treatment heat through the keratinous fibers to be bleached.

The treatment head may be moved relative to the keratinous fibers manually. As a variant, the treatment head may be moved relative to the fibers in an automated manner.

Whether or not the treatment head is stationary during the time taken for treatment of a given region, the direction in which the light pulses are emitted relative to the keratinous fibers may be varied so as to perform a scanning movement over the keratinous fibers.

Such a scanning movement, obtained by modifying the orientation of the beam directed toward the keratinous fibers over the course of time, may if necessary be combined with a movement of the treatment head relative to the keratinous fibers.

The scanning movement may also be performed, for example, without necessarily modifying the orientation of the light beam directed toward the keratinous fibers, by using a optical fiber ribbon illuminated sequentially.

No matter how the scanning is performed, this may for example take place in a first direction and the movement of the treatment head relative to the keratinous fibers may take place in a second direction, approximately perpendicular to the first. The scanning speed in the first direction may depend on the scanning speed in the second direction, and vice versa.

At least two different regions of keratinous fibers may be bleached differently.

The bleaching may thus be carried out non-uniformly on the keratinous fibers, so as to create effects. For example, the bleaching may be carried out in discrete regions, which may be arranged like points in a grid for example. It is thus possible, for example, to expose the keratinous fibers selectively so as to produce a grid pattern. The bleaching may be carried out in the form of a checkerboard or in another pattern. It is also possible to interpose, in the path of the light, a mask for forming a pattern of predetermined outline on the keratinous fibers.

It is also possible to achieve a desired degree of bleaching by treating the keratinous fibers only partially, so that regions having different degrees of bleaching are juxtaposed. These regions, which have different colors on a microscopic scale, may, when observed from a certain distance, no longer be individually discernible by the naked eye and may generate an intermediate color by color mixing.

A head of hair may be bleached in a graded fashion, for example by modifying the spatial frequency and/or the size of the regions bleached by exposure to the light pulses.

Once the bleaching has been carried out, it is then possible, where appropriate, to dye the keratinous fibers.

The keratinous fibers that have been bleached may be keratinous fibers that have their natural color or that have already been artificially dyed.

In the case of treating a head of hair, after a lock of hair has been bleached it is possible to keep this isolated from the rest of the head of hair for the time needed to dye the lock of hair.

Independently of or in combination with the foregoing, the subject of the invention is also a method of cosmetically treating keratinous fibers, especially hair fibers, comprising at least one step of at least partially bleaching the keratinous fibers, during which step at least one region to be treated is exposed to at least one light pulse, the duration over which the light power of the pulse reaching the fibers is equal to or greater than one half of its peak power being between about 100 ps and about 1 the light pulse being for example emitted by a diode-pumped laser or by a regenerative amplifier laser.

A further subject of the invention, independently of or in combination with the foregoing, is a method of at least partially bleaching keratinous fibers, in which one and the same region of fibers is exposed to light pulses emitted with a frequency of greater than 10 Hz, or greater than 100 Hz, or even greater than 1 kHz or 5 kHz.

A high frequency makes it possible for the keratinous fibers to be rapidly scanned by the light beam and, if so desired, allows progressive bleaching of the head of hair to be readily achieved. Scanning at a high frequency allows the light at each pulse to be concentrated on a very small region, and therefore provides a relatively high surface density.

A further subject of the invention, independently of or in combination with the foregoing, is a method of bleaching keratinous fibers in which the keratinous fibers are exposed to light pulses so as to create, on a microscopic scale, an alternation of regions having different degrees of bleaching, the largest dimension of the bleached regions being, for example, less than 5 mm, or less than 1 mm or even less than 100 µm, or even smaller still.

Such a method makes it possible to produce grid patterns or graded bleaching, or to achieve a given color by color mixing in regions having different degrees of bleaching. The implementation of such a method is facilitated by the use of a diode-pumped laser or a regenerative amplifier laser, although other lasers could be used.

Yet another subject of the invention, independently of or in combination with the foregoing, is a method of bleaching keratinous fibers in which the keratinous fibers are subjected to light pulses emitted by a treatment head in order to bleach them, which method may be characterized in that the emission of the pulses is synchronized with the movement of the treatment head relative to the keratinous fibers.

Yet another subject of the invention, independently of or in combination with the foregoing, is a system for optically bleaching keratinous fibers, especially hair fibers, comprising:
 a regenerative amplifier laser or diode-pumped laser for emitting light pulses; and
 a treatment head designed to expose keratinous fibers to the light pulses generated by the laser.

The laser may be configured in such a way that the duration of a light pulse is between about 1 ns and about 100 ns, for example being around 10 ns.

The bleaching system may include a device for focusing the light beam emitted by the laser. This may allow a less powerful, and therefore less expensive, laser to be used, while still achieving an energy level sufficient to destroy the melanin selectively.

If required, this focusing device may be adjustable, so as to allow the surface energy density reaching the keratinous fibers to be adjusted, this adjustment being made, for example, in accordance with the initial color of the keratinous fibers to be treated or with the desired degree of bleaching. The focusing device may be manually or automatically adjustable.

The bleaching system may include an optical deflector for making a light beam scan the region to be treated without the treatment head being moved relative to the keratinous fibers. This scanning may take place for example in a direction approximately perpendicular to the direction of movement of the treatment head relative to the keratinous fibers.

The optical deflector may for example include a movable mirror off which the light beam is reflected before it reaches the keratinous fibers or before it reaches the optical fibers conducting the light to the keratinous fibers.

Where appropriate, the optical deflector does not have to be carried by the treatment head but may be connected to the latter via an optical fiber ribbon. Such a ribbon may comprise, for example, between 2 and 5000 optical fibers, or better still between 20 and 500 optical fibers. The fibers of the ribbon may be illuminated sequentially by the light coming from the optical deflector. Thus, the light energy may be concentrated on a small number of optical fibers, or even on a single optical fiber, during emission of a light pulse.

The bleaching system may include at least one actuator for moving the treatment head relative to the keratinous fibers.

The laser may or may not be rigidly linked to the treatment head. In particular, the laser may be optically connected to the treatment head via a flexible lead. The latter may comprise at least one optical fiber.

The treatment head, especially when the laser is rigidly connected to it, may comprise at least one lens, especially a cylindrical lens, for generating an approximately flat light beam, for example one several millimeters in length by one millimeter in width. The treatment head may be designed so as to allow easy movement in a direction perpendicular to the long side of this flat light beam. The treatment head may thus include, for example, a handle, the longitudinal axis of which is approximately perpendicular to said long side.

The bleaching system may include detection means for determining the speed of movement of the keratinous fibers exposed to the light pulses relative to the treatment head and calculation means for determining the power and/or the number and/or the frequency of the light pulses in accordance with this speed of movement.

The speed of movement of the keratinous fibers relative to the treatment head may be measured in many ways.

The treatment head may for example include at least one rotary member that rotates when the keratinous fibers are moved relative to the treatment head, for example this rotary member rolling in contact with the keratinous fibers. The bleaching system may be designed to trigger the pulses according to the rotation of the rotary member, so as for example to avoid one and the same region of keratinous fibers being exposed to more than a predefined number of light pulses during the same pass.

The treatment head may also include, for example, an image analysis device for detecting the movement of the treatment head relative to the keratinous fibers or relative to a mark that is fixed relative to the keratinous fibers, for example a cord placed within or alongside a lock of hair to be bleached.

The bleaching system may include a device for analysing the color of the keratinous fibers and may be designed to prevent a further exposure to the light pulses of keratinous fibers for which the color analysis device indicates that sufficient bleaching has already been achieved.

The bleaching system may include a detection device, for example for verifying that keratinous fibers are present in front of the treatment head and be designed to prevent light pulses from being emitted when no keratinous fibers to be bleached are present.

The bleaching system may include acquisition means for entering a desired degree of bleaching, the initial color of the keratinous fibers or the desired final color after bleaching.

The bleaching system may include calculation means for automatically determining, according to the desired color of the keratinous fibers after bleaching at least one of the following: the number of light pulses; the frequency of the pulses; the surface energy per pulse.

The treatment head may include various structures for receiving and guiding the keratinous fibers, especially a lock of hair, to be bleached.

The treatment head may for example include a groove in which a lock of hair to be treated may be engaged. This groove may be formed for example between two branches. These branches are for example approximately parallel and present at one end of the treatment head.

The bleaching system may include means for simultaneously exposing two opposed faces of a lock of hair to the light pulses. These means may for example comprise means for splitting the light emitted by the laser, for taking it into each of the branches and then for projecting it onto the keratinous fibers.

The bleaching system may include, if required, means for determining the thickness of the lock of hair exposed to the light pulses and may be designed so as to calculate, especially in accordance with this thickness, the power and/or the number and/or the frequency of the light pulses.

These means may comprise, for example, a sensor for detecting the light remaining after having passed through the keratinous fibers.

The bleaching system may include means, for example a scanner for reading an image to be reproduced on the head of hair.

The bleaching system may also include display means for displaying a simulation of a bleaching result, for example a screen on which an image is displayed. The bleaching system may include means for selecting an image and means for determining a bleaching treatment to be carried out on the head of hair so as to obtain a head of hair corresponding to the image selected.

The bleaching system may include means for keeping a lock of hair isolated, after it has been exposed to the light pulses, ready for a subsequent treatment, especially a dyeing treatment. These means may consist of the treatment head itself, especially when this has two branches between which the lock of hair is engaged.

The treatment head may include an application member capable of applying a substance to the keratinous fibers, for example to a lock of hair. This application member comprises for example an ink pad.

The treatment head may be designed so that the application of the aforementioned substance by the application member takes place after the keratinous fibers have been exposed to the light pulses. The substance may be a hair dye product and/or a hair care product.

The treatment head may include means for combing out a lock of hair before and/or after it has been introduced into the treatment head.

The bleaching system may include a mask for defining the extent of the treated region. The bleaching system may include means for cooling this mask. These cooling means may for example comprise a fan or a cooling circuit in which a fluid, especially water, circulates.

The bleaching system, and especially the treatment head, may include a screen for absorbing the light remaining after having passed through the keratinous fibers.

The bleaching system may be devoid of means for cooling the keratinous fibers by blowing a stream of gas over them.

Yet another subject of the invention, independently of or in combination with the foregoing, is a system for bleaching keratinous fibers, especially hair fibers, comprising:
  a laser for emitting light pulses; and
  a treatment head designed to receive at least one lock of hair to be at least partially bleached and for exposing this lock of hair to the light pulses, the laser being configured in such a way that the duration of a light pulse is between about 100 ps and about 1 µs.

The frequency of the light pulses is advantageously greater than 1 kHz. The duration of a light pulse is for example greater than 5 ns.

The keratinous fibers treated may or may not be dry, for example they may be damp or wet.

The invention may be better understood on reading the following detailed description of non-limiting examples of its implementation and on examining the appended drawing, in which:

FIGS. 5 and 6 are schematic partial views in longitudinal section and cross section, respectively, of the treatment head of the system of FIG. 1;

FIG. 7 is a schematic partial view of a lock of hair;

FIG. 8 illustrates schematically and partially the use of the system of FIG. 1;

FIGS. 10 to 13 are schematic partial views of alternative embodiments of treatment heads according to the invention;

FIG. 14 illustrates an example of a cross section of the light beam coming from the treatment head of FIG. 13;

FIGS. 15 to 18 are schematic partial cross-sectional views of alternative embodiments of treatment heads according to the invention;

Figure 1:
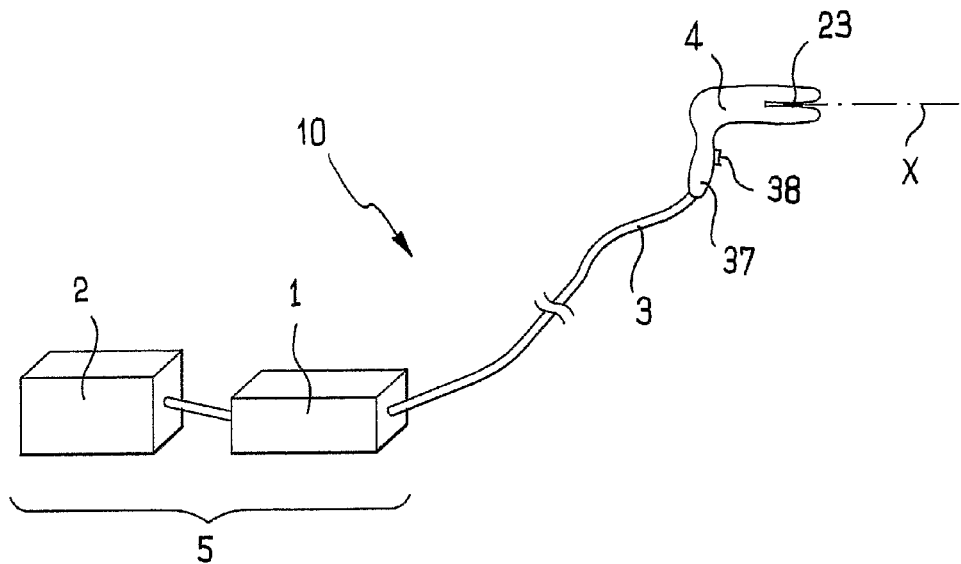
FIG. 1 is a schematic partial view of a bleaching system produced in accordance with the invention.

FIG. 1 shows a system 10 for bleaching keratinous fibers, which comprises a base unit 5 made up of a laser 1 and a power supply 2, the light pulses emanating from the laser 1 being transmitted via a flexible lead 3 to a treatment head designed to receive at least one lock of hair. Where appropriate, the laser 1 and the power supply 2 may form a one-piece assembly. The base unit 5 may also include or be connected to, as will be seen later, calculation means, that include a microcomputer and/or one or more specific microprocessors or microcontrollers and the associated components.

The treatment head 4 may include, as illustrated, a handle 37 and a pushbutton 38 for triggering the emission of the light pulses.

The laser 1 may for example be a diode-pumped laser or a regenerative amplifier laser.

Figure 2:
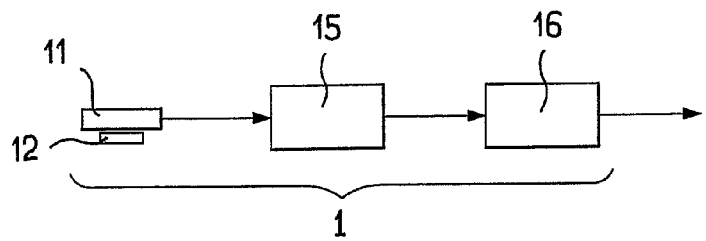
FIG. 2 is a schematic view of a laser that can be used in the system of FIG. 1.

If the laser 1 is a diode-pumped laser, this may comprise, as illustrated in FIG. 2, an excitable rod 11, shown highly schematically in this figure, formed for example from a matrix of lithium yttrium fluoride ($LiYF_4$) doped with neodymium ions ($Nd^{3+}$). Of course, it would not be outside the scope of the present invention to use a different material to form the excitable rod 11, for example if a matrix is made of yttrium aluminum garnet doped with neodymium ions.

FIG. 2 shows very schematically at least one pump laser diode 12 that illuminates the excitable rod 11, the diode-pumped laser preferably having several pump laser diodes 12 uniformly distributed along the excitable rod 11, in opposed pairs. The excitable rod 11 is for example of parallelepipedal shape, a few centimeters in length and with sides of a few millimeters.

As an example of a diode-pumped laser, mention, may be made of that with the reference QG523-500 from BFI Optilas, with a power of 500 mW.

In the case of a diode-pumped laser, the excitable rod 11 may for example emit at a wavelength of about 1046 nm, but it would not be outside the scope of the present invention if the wavelength of the laser radiation emitted by the rod 11 were to be other than this.

The light emitted by the excitable rod 11 may pass, as seen in FIG. 2, through a frequency doubler 15, known per se, integrated into the laser 1, allowing the exiting wavelength to be halved. Where appropriate, it is possible for the frequency doubler 15 not to be integrated into the laser 1.

The frequency doubler 15 makes it possible to obtain light pulses of 523 nm wavelength in the example in question, but it would not be outside the scope of the present invention if the wavelength of the light emitted at the exit of the frequency doubler 15 were to be other than this, for example between about 400 and about 700 nm, better still between about 400 and about 600 nm and even better still between about 400 and about 550 nm. If necessary, an infrared filter 16, which may be integrated into the laser 1, can be used to remove the residual 1064 nm wavelength radiation output by the frequency doubler 15.

Figure 3:
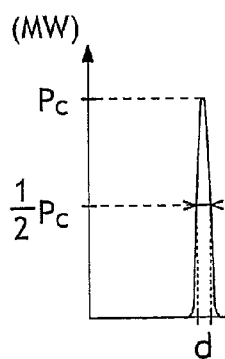
FIG. 3 shows schematically the variation in power of a pulse emitted by a diode-pumped laser as a function of time.

The laser 1 emits light pulses of peak power $P_c$ and duration d, the duration of a light pulse being defined within the context of the present invention by the time during which the light power of the pulse is equal to or greater than one half of its peak power $P_c$, as illustrated schematically in FIG. 3. The peak power $P_c$ is for example less than 100 MW/cm$^2$, especially less than 10 MW/cm$^2$.

The duration d of a light pulse emitted by the laser 1 is for example greater than 5 ns, especially about 10 ns, but it would not be outside the scope of the present invention for it to be different, for example between about 100 ps and about 1 μs, better still between about 1 ns and about 100 ns.

The flexible lead 3 may include at least one optical fiber. This is for example a step-index multimode fiber, for example with the reference TCL-MA100H CF 04406-11 from SEM, having a pure silica core 100 μm in diameter, a numerical aperture of 0.22 and a maximum power of 1 GW/cm$^2$.

The flexible lead 3 may also include one or more electrical cables for data exchange between the treatment head 4 and the base unit 5. The flexible lead 3 may especially include a cable for a signal representative of pressure on the control button 38 to be sent to the base unit 5.

Figure 4:
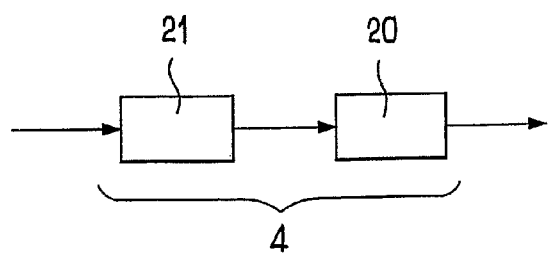
FIG. 4 is a schematic partial view of the treatment head of the system of FIG. 1.

The treatment head 4 may include an optical deflector 20, shown schematically in FIG. 4, allowing the light that it receives to be deflected so that at least one fraction of the region to be bleached, presented to the treatment head 4, is scanned.

This optical deflector 20 may comprise a movable mirror, especially a swivel mirror. One possibly suitable deflector 20, known by the reference SC-5 and having the EOPC brand name, has a mirror with sides of 10 mm, allows 100 Hz frequency scanning and has a ±20° angle characteristic.

The bleaching system 10 may include a focusing device 21 placed in the light path between the exit of the excitable rod 11 and the keratinous fibers to be treated, so as to increase the surface energy of the light beam directed onto the keratinous fibers and, where appropriate, to allow the surface energy density to be adjusted.

Such a focusing device 21 is for example incorporated into the treatment head 4, as illustrated in FIG. 4, being located for example upstream of the optical deflector 20.

The focusing device 21 comprises for example a convergent lens, but it would not be outside the scope of the present invention for this to be some other focusing device comprising one or more convergent lenses or having other properties.

The focusing device 21 may optionally, as mentioned above, allow the surface energy level of the light reaching the keratinous fibers to be adjusted.

The focusing device 21 may for example comprise a lens that can be placed so that light is more or less focused on the keratinous fibers and/or so that the light beam emanating from the laser 1 is widened to a greater or lesser extent.

Such a lens may be moved manually or automatically.

If the lens is moved manually, it is for example driven, so as to move axially, by the rotation of a ring or by the movement of a cursor. This ring or this cursor may for example be associated with gradations corresponding to different energy levels or to particular hair colors.

If the lens is moved automatically, for example by an electric servomotor, this movement may have been calculated by the bleaching system in accordance with a bleaching result to be achieved or according to an initial hair color, for example.

The treatment head 4 is designed to receive a lock of hair M to be at least partially bleached and to expose this lock of hair M to the light pulses emanating from the laser 1.

For this purpose, the treatment head 4 may include any means for receiving and guiding the hair, for example, as may be seen in FIGS. 1, 5 and 6, a groove 23 formed between an upper branch 26 and a lower branch 27, both branches lying parallel to the axis X.

At least one of the branches, for example the lower branch 27, has, on its face 27a facing the other branch, an exit window 28 that allows the light to reach the fibers to be treated. One or more mirrors 25 or other light-guiding elements may be placed inside the treatment head 4 so as to suitably direct the light pulses onto the exit window 28.

The treatment head 4 may have only a single exit window 28 on one of the branches, the other branch then constituting a screen for absorbing the residual light passing through the lock of hair M.

As a variant, the treatment head 4 may include means for simultaneously exposing at least two opposed faces of the lock of hair M to the light pulses.

For this purpose, the treatment head 4 may include a second exit window on the face 26a of the upper branch 26 facing the lower branch 27 and means for splitting the laser radiation into two beams, so that the light pulses are emitted from each branch 26 or 27 onto the keratinous fibers. For example, these means may comprise at least one semireflecting surface or several optical fibers.

If required, each branch 26 or 27 is supplied alternately with the light emanating from the laser 1. To supply the branches 26 and 27 alternately, the optical deflector 20 may for example deflect the light alternately onto one of the branches 26 and 27 and then onto the other, or as an alternative onto two optical fibers conducting the light to the output windows.

The target area A, able to receive the light from the laser 1 when the treatment head 4 is stationary relative to the keratinous fibers, may have a shape that depends for example on the shape of the light beam reaching the keratinous fibers and, if appropriate, on the characteristics of the optical deflector 20.

The target area A has for example a rectangular outline as illustrated in FIG. 7, the long side of which is for example directed approximately perpendicularly to the X axis.

The treatment head 4 may be provided with cooling means for cooling the lock of hair M by blowing a stream of gas onto the hair, when the heating induced by the laser light risks damaging the hair.

The bleaching system 10 may be used as follows.

A lock of hair M is introduced into the groove 23 so as to bring a portion of it opposite the exit window 28, as illustrated in FIG. 8.

When the laser 1 is operating, the keratinous fibers are at least partly exposed to at least one light pulse.

The light emitted by the laser 1 during a pulse may form for example a light spot 31 within the target area A, as shown in FIG. 7. This light spot 31 corresponds for example to only a fraction of the extent of the target area A, for example less than 1% of the width of the latter. As a variant, the light spot 31 may represent a larger fraction of the extent of the target area A and, at most, the light spot 31 may cover the entire target area A.

The light spot 31 formed has for example one dimension, measured along the scanning direction $D_1$ of FIG. 7, between about 20 μm and about 100 μm, for example around 50 μm.

The dimensions of the light spot 31 may for example depend on the number of adjacent points of impact that it is desired to form on the keratinous fibers during a cycle of scanning the target area A due to the optical deflector 20. Thus, it is possible to scan a width of 1 cm by juxtaposing, in the direction $D_1$, 125 points of impact of a light spot 31 having sides of 80 μm in said direction.

The shape of the light spot 31 may for example be substantially polygonal, especially square, or otherwise. Its largest dimension may be up to several millimeters, if required.

The scanning of the target area A by the light beam, coming from the treatment head and due to the reflector 20, is for example carried out in the direction $D_1$, perpendicularly to the direction of movement $D_2$ of the treatment head 4 relative to the lock of hair M, i.e. in a direction approximately parallel to the X axis in the example shown in FIG. 8.

Depending on the ratio of the scanning frequency to the laser light pulse emission frequency, the same region of the target area A may be exposed in succession to more than one light pulse during a scanning cycle, that is to say when the light spot 31 is shifted along the direction $D_1$ by a distance corresponding to the long side of the target area A in the example shown in FIG. 7. For example, for a 100 Hz scanning frequency and a 100 Hz light pulse frequency, substantially no region of the target area A is exposed more than once over the course of a scanning cycle. For the same scanning frequency and a light pulse frequency of 1 kHz, any one region of the target area A is exposed approximately ten times. The number of pulses to which any one region is exposed may be determined according to the surface energy, or vice versa, for example using logarithmic laws such as those that will be explained in detail later, it being possible for these laws to involve the laser light pulse emission frequency.

Thus, for a scanning frequency of 100 Hz and a light pulse frequency of 100 Hz also, the surface energy reaching the fibers is preferably between 0.2 J/cm² and 30 J/cm² for chestnut brown hair. For a scanning frequency of 100 Hz and a pulse frequency of 1 kHz, the surface energy is preferably between 0.06 J/cm² and 5 J/cm².

The bleaching of the keratinous fibers may or may not be uniform.

The bleaching system 10 may for example be designed so as to bring light pulses only into certain regions of the target area A at each scanning cycle, so that at least two keratinous fibers lying therein are bleached differently.

For example, it is possible to illuminate only certain regions of the target area A so as to obtain an intermediate shade between the initial color of the lock of hair and white.

It is also possible for the head of hair to undergo graded bleaching.

In order to obtain graded bleaching in the direction $D_2$ in FIG. 7, the surface energy density received by the keratinous fibers may for example be increased while the treatment head is being moved along said fibers, for example by acting on the focusing device 21.

It is also possible to make several passes and to make the number of passes depend on the position of the treatment head 4 on the hair.

The speed with which the treatment head 4 is moved relative to the keratinous fibers may also be varied, a slow movement allowing the keratinous fibers to be exposed to a higher energy than a rapid movement.

Figure 9:
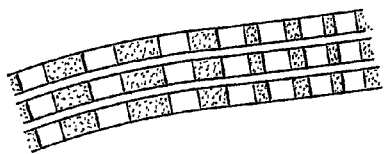
FIG. 9 shows schematically and partially an example of a bleaching effect that can be obtained on a lock of hair.

The dimensions of the bleached regions, which alternate with unbleached regions, may also be varied, as illustrated schematically in FIG. 9.

In general, the surface energy of the light reaching the keratinous fibers and the number of light pulses to which the keratinous fibers will be exposed may depend on the initial color of the fibers.

The data given below are in particular valid for chestnut brown hair, especially of shade 4 in the European Classification. These values may be modified in order to adapt the bleaching treatment to darker or lighter hair.

If a region to be bleached receives a single light pulse, the surface energy of the single pulse may be greater than 0.2 J/cm² or even greater than 0.5 J/cm². The surface energy of the single pulse remains less than 30 J/cm².

If the number of light pulses received by one and the same region is between 2 and 10, the surface energy of a pulse may be equal to or greater than 0.06 J/cm² or even equal to or greater than 0.12 J/cm². The surface energy per pulse may be equal to or less than 5 J/cm².

If the number of pulses received by one and the same region is between 11 and 100, the surface energy of a pulse may be equal to or greater than $0.12/(\log(f)+1)$ J/cm² or even greater than $0.24/(\log(f)+1)$ J/cm², f being the frequency of the pulses. The surface energy per pulse may be equal to or less than $6/(\log(f)+1)$ J/cm², or even equal to or less than $4/(\log(f)+1)$ J/cm².

If the region is exposed to more than 100 pulses, the surface energy per pulse may be equal to or greater than $0.06/(\log(f)+1)$ J/cm² or even equal to or greater than $0.12/(\log(f)+1)$ J/cm². The surface energy per pulse may be equal to or less than $2.4/(\log(f)+1)$ J/cm² or even equal to or less than $1.2/(\log(f)+1)$ J/cm².

The frequency of the light pulses will preferably be relatively high, which especially allows greater progressivity in the effects obtained.

The laser 1 is for example designed so that the frequency of the emitted pulses is around 10 kHz.

The treatment head 4 mentioned above has a groove 23 formed between the two branches 26 and 27, but it would not be outside the scope of the present invention if the treatment head 4 were to be configured in a different manner in order to expose the keratinous fibers to the light emitted by the laser.

Figures 10, 11:
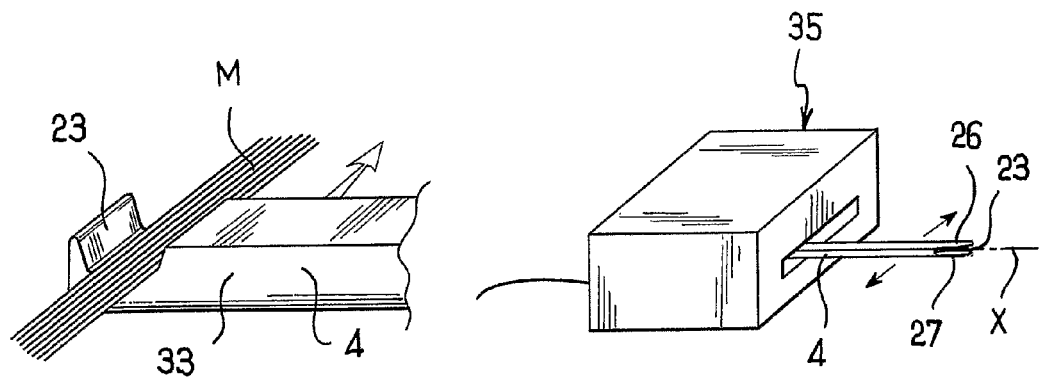

FIG. 10 illustrates schematically a treatment head 4 having a groove 23 formed on only one branch 33.

In this example, the treatment head 4 has no screen for absorbing the residual light passing through the lock of hair M.

In the example shown in FIG. 1, the treatment head 4 is moved manually relative to the hair, but it would not be outside the scope of the present invention if the treatment head 4 were to be moved automatically relative to the keratinous fibers.

By way of example, FIG. 11 shows very schematically a treatment head 4 connected to an actuator 35 for moving it translationally perpendicular to the X axis.

The emission of the pulses may be controlled according to the movement of the treatment head 4 relative to the hair.

In all the examples that have just been described, the laser 1 is separate from the treatment head 4, being linked to the latter via the flexible lead 3, and the treatment head 4 incorporates the optical deflector 20.

It would not be outside the scope of the present invention if the deflector 20 were not to be incorporated into the treatment head 4.

Figure 12:
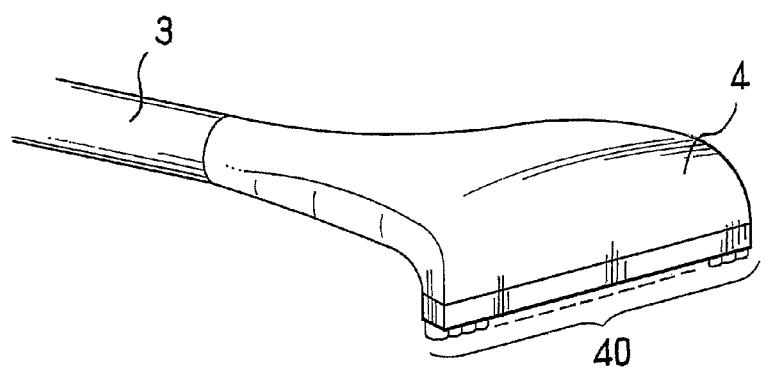

As an example, FIG. 12 shows, schematically and partially, a bleaching system in which the optical deflector 20 is optically linked to the treatment head 4 via an optical fiber ribbon 40.

This optical fiber ribbon 40 is for example a ribbon with the reference FC-10 of the EOPC brand, comprising seventy fibers 140 μm in diameter, allowing a width of approximately one centimeter to be covered using the treatment head 4.

Of course, it would not be outside the scope of the present invention if the number of optical fibers forming the ribbon were to be different, for example between 20 and 500.

Thanks to the optical deflector 20, the optical fibers of the ribbon 40 may be supplied sequentially with the light emanating from the laser 1.

The laser 1 may also be integrated into the treatment head 4, which may furthermore include, as illustrated in FIG. 13, a focusing device 21.

The focusing device 21 may comprise, for example, at least one cylindrical lens for forming a light beam of very elongate, especially substantially rectangular, cross section, as illustrated in FIG. 14. This beam may form, on the keratinous fibers, an approximately rectangular spot of more than one millimeter in length, for example about 3 mm in width, and less than one millimeter in width, for example less than 10 μm in width, for example about 3 μm in length. The elongate shape of the light spot formed by such a beam dispenses with the use of an optical deflector 20.

Of course, it would not be outside the scope of the present invention if the treatment head 4 were also to include an optical deflector 20.

The bleaching system 10 may include means for combing out the lock of hair M before and/or after it has been introduced into the treatment head 4. Where appropriate, these combing means may include raised features that are transparent to the light received by the keratinous fibers.

The treatment head 4 may especially have one or more teeth 44 or other raised features placed in front of and/or behind the groove 23, as illustrated schematically in FIG. 15.

The treatment head 4 may include means for determining the speed of movement of the lock of hair M exposed to the light pulses relative to the treatment head. These means may for example comprise at least one rotary member that rotates through the effect of the movement of the lock of hair M in the treatment head so as to allow the bleaching system to automatically calculate, according to this speed of movement, the power and/or the number and/or the frequency of the light pulses and/or to synchronize the triggering of the pulses with the movement of the lock of hair M.

As an example, FIG. 16 shows a treatment head 4 having two opposed rollers 45 that can rotate in contact with the lock of hair M introduced between them.

The rotation of the rollers 45 is detected and the bleaching system includes calculation means, comprising for example a microcomputer or any electronic circuit suitable for varying the emission of the light pulses according to this rotation.

The triggering of the light pulses may for example take place in the example shown in FIG. 7 such that the target areas A exposed during two consecutive scanning cycles are juxtaposed along the direction $D_2$.

The bleaching system 10 may furthermore include means for preventing the same region of fibers from being subjected twice to more than a predefined number of pulses when the treatment head 4 is stationary relative to the keratinous fibers, so as not to damage them.

For this purpose, the bleaching system 10 may include at least one device for measuring the color of the fibers. In the example illustrated in FIG. 17, the color of the keratinous fibers is determined using a camera 47 housed in the treatment head 4, as shown schematically therein. Of course, it would not be outside the scope of the present invention if this camera 47 were to be replaced with any other suitable color detector.

The image produced by the camera 47 is for example analysed so as to determine the degree of bleaching of the keratinous fibers within the target area A. Emission of the light pulses is stopped when the desired degree of bleaching has been achieved.

The camera 47 may also be used to verify the presence of a lock of hair M to be treated.

The camera 47 may also be used to determine the speed of movement of the keratinous fibers relative to the treatment head, by analysing the speed of movement of the boundary between the bleached and unbleached regions relative to the treatment head 4.

The treatment head 4 may furthermore be designed so that the hair can be dyed progressively as the lock of hair M is moved.

For this purpose, the treatment head 4 may include an application member 50, comprising for example an ink pad for depositing a hair dye onto the lock of hair M. In the example illustrated, this ink pad is carried by a support that does not impede the passage of the lock of hair M between the branches 26 and 27.

A product other than a hair dye may also be applied, for example a hair smoother. A product insensitive to the wavelength of the light received by the keratinous fibers or on the contrary activated by this light may also be applied to the fibers before the bleaching treatment, for example in order to facilitate the treatment or to obtain a particular shade.

Figure 19:
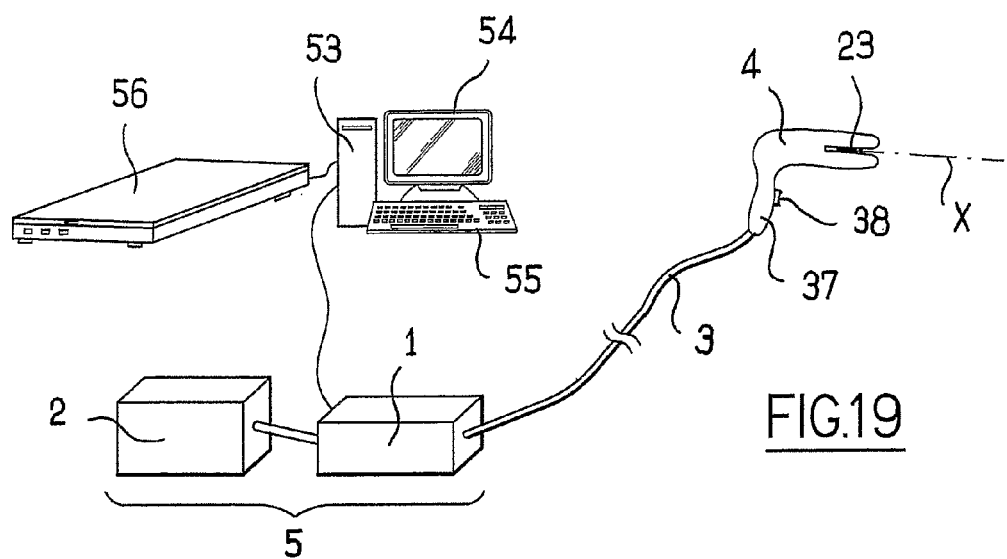
FIG. 19 is a schematic partial view of an alternative embodiment of a bleaching system according to the invention.
Figure 20:
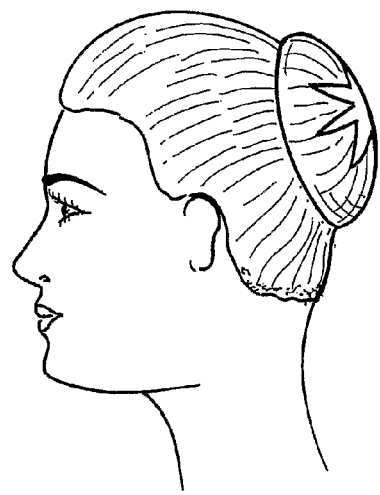
FIG. 20 illustrates, schematically, an example of a bleaching effect obtained on a head of hair with the use of a mask.

The bleaching system 10 may also include calculating means 53, a screen 54 and a keyboard 55 as shown in FIG. 19. The keyboard may be used to input the initial color of the fibers, the desired degree of bleaching or the desired final color after bleaching, but other acquisition means may be used, for example a scanner 56 or a camera, for example the aforementioned camera 47. The latter may be used to measure the initial color of the keratinous fibers.

The calculating means 53 may comprise a microcomputer or other computing or electronic means, which are integrated into or linked to the base unit 5, or distributed between the two.

The calculating means 53 may be designed to act on the emission of the light pulses, especially their triggering, their frequency and/or their power, and also on the optional optical deflector 20, especially its orientation, and on the optional focusing device 21 and/or to process data coming from the treatment head 4, this data coming for example from the control button 38 of the optional camera 47, or being linked to other sensors integrated into the treatment head, for example for detecting the rotation of the optional rollers 45.

The calculating means 53 may be programmed to automatically determine at least one of the following: the number of pulses; the frequency of the pulses; and the surface energy per pulse, for example according to the final color of the fibers after bleaching and/or the initial color of the fibers.

The screen 54 may be used to display, before the treatment, the hair that will be obtained after the bleaching treatment, for example in the form of a 2D or 3D image.

The calculating means 53 may also be used to select an image of the hair that is desired and to determine the bleaching treatment to be carried out on the hair to be treated so that hair conforming to the selected image is obtained, especially when a pattern is to be formed on the hair.

The pattern selected may be in a library of images stored in a memory, or it may come from reading in a photograph, for example by means of the scanner 56. It is thus possible, for example, to input, using the scanner 56, an image, for example a logo, and to draw this logo on the hair by selectively bleaching it.

A mask for forming a pattern of predetermined shape on the keratinous fibers may be interposed in the path of the light emanating from the treatment head.

Figure 21:
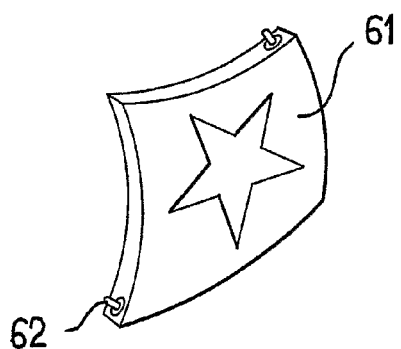
FIG. 21 illustrates, schematically and partially, a mask that can be used to obtain the bleaching result shown in FIG. 20.

The mask may include, as illustrated in FIG. 21, cooling means 62 such as, for example, a water cooling circuit or a fan.

In what has been described above, the lock of hair M is composed of natural hair fibers, but it would not be outside the scope of the present invention if the bleached keratinous fibers were to be animal fibers or human keratinous fibers other than hair.

Alternative embodiments (not illustrated) of the invention may combine features taken from the various embodiments that have been described here.

Throughout the description, and including the claims, the expression "comprising a" or "including a" should be understood to mean "comprising at least one" or "including at least one", unless specified otherwise.

The invention claimed is:

1. A method of treating keratinous fibers for at least partially bleaching the keratinous fibers, comprising: exposing at least one region being treated to at least one light pulse laser, a duration over which a light power of the pulse reaching the fibers is equal to or greater than one half of a peak power being between about 100 ps and about 1 μs, the pulses occurring at a frequency greater than about 10 kHz.

2. The method as claimed in claim 1, the duration of the light pulse reaching the keratinous fibers being between about 1 ns and about 100 ns.

3. The method of claim 2, wherein the duration is between about 1 ns and about 50 ns.

4. The method as claimed in claim 1, wherein the at least one region is exposed to a single pulse for a given region to be treated.

5. The method as claimed in claim 4, a surface energy of the single pulse being greater than $0.2$ J/cm$^2$.

6. The method as claimed in claim 4, a surface energy of the single pulse being greater than $0.5$ J/cm$^2$.

7. The method as claimed in claim 4, a surface energy of the single pulse being less than $30$ J/cm$^2$.

8. The method as claimed in claim 1, wherein the at least one region to be treated is exposed to a number of light pulses ranging between 2 and 10.

9. The method as claimed in claim 8, a surface energy of a pulse being equal to or greater than $0.06$ J/cm$^2$.

10. The method as claimed in claim 9, the surface energy of a pulse being equal to or greater than $0.12$ J/cm$^2$.

11. The method as claimed in claim 8, the surface energy per pulse being equal to or less than $5$ J/cm$^2$.

12. The method as claimed in claim 1, wherein the at least one region to be treated is exposed to a number of pulses ranging between 11 and 100.

13. The method as claimed in claim 12, a surface energy of a pulse being equal to or greater than $0.12/(\log(f)+1)$ J/cm$^2$, f being a frequency of the pulses.

14. The method as claimed in claim 12, a surface energy of a pulse being greater than $0.24/(\log(f)+1)$ J/cm$^2$, f being a frequency of the pulses.

15. The method as claimed in claim 12, a surface energy per pulse being equal to or less than $6/(\log(f)+1)$ J/cm$^2$, f being a frequency of the pulses.

16. The method as claimed in claim 12, a surface energy per pulse being equal to or less than $4/(\log(f)+1)$ J/cm$^2$, f being a frequency of the pulses.

17. The method as claimed in claim 1, the at least one region to be treated being exposed to a number of pulses greater than 100.

18. The method as claimed in claim 17, a surface energy per pulse being equal to or greater than $0.06/(\log(f)+1)$ J/cm$^2$, f being a frequency of the pulses.

19. The method as claimed in claim 17, a surface energy per pulse being equal to or greater than $0.12/(\log(f)+1)$ J/cm$^2$, f being a frequency of the pulses.

20. The method as claimed in claim 11, a surface energy per pulse being equal to or less than $2.4/(\log(f)+1)$ J/cm$^2$, f being a frequency of the pulses.

21. The method as claimed in claim 12, a surface energy per pulse being equal to or less than $1.2/(\log(f)+1)$ J/cm$^2$, f being a frequency of the pulses.

22. The method as claimed in claim 1, a peak surface power of a light pulse emitted by the laser and received by the keratinous fibers being equal to or less than $100$ MW/cm$^2$.

23. The method as claimed in claim 22, the peak surface power being less than $10$ MW/cm$^2$.

24. The method as claimed in claim 23, the peak surface power being less than $1$ MW/cm$^2$.

25. The method as claimed in claim 1, a wavelength of the light reaching the keratinous fibers being between about 400 nm and about 700 nm.

26. The method as claimed in claim 1, a wavelength of the light reaching the keratinous fibers being between about 400 nm and about 600 nm.

27. The method as claimed in claim 1, a wavelength of the light reaching the keratinous fibers being between about 400 nm and about 550 nm.

28. The method as claimed in claim 25, a wavelength of the light reaching the keratinous fibers being around 523 nm.

29. The method as claimed in claim 1, wherein at least one of the following: a number of pulses reaching a given region to be treated; a frequency of the pulses; and a surface energy per pulse, is determined in accordance with an initial color of the keratinous fibers to be treated.

30. The method as claimed in claim 1, at least one of the following: a number of pulses reaching a given region to be treated; a frequency of the pulses; and a surface energy per pulse, being determined in accordance with a desired color of the keratinous fibers after treatment.

31. The method as claimed in claim 1, the treatment being assisted by a device for analysing a color of the keratinous fibers.

32. The method as claimed in claim 1, the light pulses being emitted by a treatment head that is moved relative to the keratinous fibers when the treatment passes from a first treatment region to a second treatment region.

33. The method as claimed in claim 32, the emission of light pulses being triggered according to movement of the treatment head relative to the keratinous fibers.

34. The method as claimed in claim 31, the treatment head being moved manually relative to the keratinous fibers.

35. The method as claimed in claim 1, the direction in which the light pulses emitted relative to the keratinous fibers being varied so as to perform a scanning movement over the keratinous fibers.

36. The method as claimed in claim 1, at least two different regions of the keratinous fibers being bleached differently.

37. The method as claimed in claim 1, a grid pattern being produced on a head of hair by exposing the keratinous fibers in a selective manner.

38. The method as claimed in claim 1, a head of hair being bleached in a graded fashion.

39. The method as claimed in claim 1, a mask being interposed in a path of the light, allowing a pattern of predetermined shape to be formed on the keratinous fibers.

40. The method as claimed in claim 1, the keratinous fibers being dyed after the treatment.

41. The method as claimed in claim 1, the keratinous fibers that are bleached being keratinous fibers having an artificial color.

42. The method as claimed in claim 1, wherein after a lock of hair has been bleached it is kept isolated from the rest of the head of hair for the time needed to dye said lock of hair.

* * * * *